(12) United States Patent
Yamada et al.

(10) Patent No.: US 6,261,812 B1
(45) Date of Patent: *Jul. 17, 2001

(54) PROCESS FOR PRODUCING DIGLYCERIDES

(75) Inventors: Yasushi Yamada; Masami Shimizu; Masakatsu Sugiura; Naoto Yamada, all of Ibaraki (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/070,006

(22) Filed: Apr. 30, 1998

(30) Foreign Application Priority Data

Aug. 18, 1997 (JP) .................................................. 9-221502

(51) Int. Cl.$^7$ ....................................................... C12P 7/64
(52) U.S. Cl. ............................................ 435/134; 435/135
(58) Field of Search .................................... 435/134, 135

(56) References Cited

U.S. PATENT DOCUMENTS

| | | | |
|---|---|---|---|
| 3,862,197 | 1/1975 | Castner . | |
| 4,018,806 | * 4/1977 | Wyness | 260/426 |
| 5,128,251 | * 7/1992 | Yokomichi | 435/135 |
| 5,219,744 | * 6/1993 | Kurashige et al. | 435/135 |
| 5,677,160 | * 10/1997 | Oester et al. | 435/135 |

FOREIGN PATENT DOCUMENTS

| | | |
|---|---|---|
| 0 191 217 | 8/1986 | (EP) . |
| 0 378 893 | 7/1990 | (EP) . |
| 0426 155 | 5/1991 | (EP) . |
| 0 307 154 B2 | 4/1996 | (EP) . |
| 0 836 805 | 4/1998 | (EP) . |
| 1-174384 | 7/1989 | (JP) . |
| 6 -65311 | 8/1994 | (JP) . |
| WO 96/23425 | 8/1996 | (WO) . |

OTHER PUBLICATIONS

Patent Abstracts of Japan, vol. 015, No. 068 (C–0807), Feb. 18, 1991, JP 02 295490, Dec. 6, 1990.
Patent Abstracts of Japan, vol. 017, No. 429 (C–1095), Aug. 10, 1993, JP 05 095792, Apr. 20, 1993.

* cited by examiner

*Primary Examiner*—Irene Marx
(74) *Attorney, Agent, or Firm*—Oblon, Spivak, McClelland, Maier & Neustadt, P.C.

(57) ABSTRACT

A process for producing diglycerides is provided by which high-purity diglycerides can be produced at a lower cost and more efficiently than conventional esterification and glycerolysis processes, and which inhibits the deterioration of oil quality, such as discoloration, and the loss of trace active ingredients derived from a feedstock of fats and oils, which involves partially hydrolyzing a fat or oil, followed by esterifying the resultant product with glycerol.

8 Claims, No Drawings

PROCESS FOR PRODUCING DIGLYCERIDES

BACKGROUND OF THE INVENTION

1. Field of the Invention

The present invention relates to a process for producing diglycerides which comprises partially hydrolyzing fats and oils and adding glycerol to the decomposition product to conduct esterification.

2. Discussion of the Background

Diglycerides are used as additives for improving the plasticity of fats or as bases in the fields of foods, medicines, cosmetic preparations, and the like.

Examples of processes for producing diglycerides include the esterification or transesterification method and the glycerolysis method.

A representative example of the esterification or transesterification method is disclosed in JP-B 6-65311, in which fatty acids or lower alcohol esters thereof are reacted with glycerol in the presence of an immobilized lipase having 1,3-position selectivity and the by-product water or lower alcohol formed by the reaction is removed from the system at a reduced pressure to obtain the diglycerides.

Although the esterification or transesterification method is a process in which fatty acids or lower alcohol esters thereof and glycerol are converted to partial diglycerides through a one-step reaction, it is not cost efficient because the individual feedstock materials are expensive.

When a fat is used as the feedstock, steam decomposition of the fat is generally conducted under the conditions of 50 to 60 $kg/cm^2$ and 250 to 260° C. However, the decomposition products discolor considerably and, thus, distillation is necessary. Performing a distillation treatment, in the case where a vegetable oil or the like is used as the feedstock, results in a decrease in the yield of about 10%. In addition, active ingredients, such as a phytosterol, that are present in the vegetable oil are lost as a distillation residue.

A representative example of the glycerolysis reaction in which a fat is used as the feedstock is given in JP-B 6-65310. This reference discloses an alcohol group exchange reaction between a fat and glycerol that is conducted in the presence of an immobilized lipase having 1,3-position selectivity, to obtain diglycerides. However, this method requires 10 hours or more for completion of the reaction and is unsatisfactory in industrial productivity.

SUMMARY OF THE INVENTION

Accordingly, one object of the present invention is to provide a method for efficiently producing high-purity diglycerides using relatively inexpensive fats and oils as the feedstock.

A further object of the present invention is to provide a method for producing diglycerides that inhibits the deterioration of oil quality, such as discoloration.

A further object of the present invention is to provide a method for producing diglycerides that is less expensive than conventional esterification and glycerolysis processes.

These and other objects of the present invention have been satisfied by the discovery of a process for producing diglycerides, comprising a first-stage reaction in which fats and oils are partially hydrolyzed and a second-stage reaction in which glycerol is added to the obtained decomposition product to conduct esterification.

DESCRIPTION OF THE PREFERRED EMBODIMENTS

In the present method, the first-stage reaction comprises mainly the partial hydrolysis reaction of a fat or oil.

Examples of the fats and oils useful in this invention include conventional vegetable and animal fats and oils or processed fats and oils, each having $C_{4-22}$, saturated or unsaturated fatty acid groups and mixed fats and oils thereof. For example, use may be made of rapeseed oil, soybean oil, cottonseed oil, olive oil, corn oil, coconut oil, beef tallow, lard, fish oil, etc.

Methods for the partial hydrolysis of fats and oils are not particularly limited. The partial hydrolysis can be conducted according to a conventionally known method in which partial hydrolysis is conducted after water is added, preferably in an amount of from 20 to 180 parts by weight per 100 parts by weight of the fats and oils. Other examples of suitable hydrolysis techniques include enzymatic hydrolysis and a method based on steam decomposition.

When the partial hydrolysis is conducted by the enzymatic method, the hydrolysis is preferably conducted at a temperature of from 20 to 70° C. With respect to the form of the enzyme, use can be made of an immobilized enzyme, an intracellular enzyme or an enzyme in an unimmobilized free state. Examples of suitable equipment for the enzymatic reaction include an agitation tank, a fixed bed, and a fluidized tank as well as combinations of these. The reactions can be conducted in a batchwise, continuous, or semicontinuous manner.

On the other hand, when the partial hydrolysis is conducted by the steam decomposition method, it is preferably conducted at a temperature of from 190 to 240° C., preferably from 200 to 235° C. Examples of suitable equipment for steam decomposition include an autoclave, a continuous decomposition tower, etc. Again, the reaction can be performed in a batchwise, continuous, or semicontinuous manner.

Since the present method is intended to ultimately produce diglycerides, 100% decomposition is unnecessary in the hydrolysis reaction of fats and oils at the first stage, and partial glycerides and triglycerides may be present. The reaction can be preferably controlled so that the amount of the fatty acids resulting from the decomposition may be from 67 to 96% by weight, preferably from 75 to 93% by weight. The reaction time can be shortened by subjecting the decomposition product containing partial glycerides to esterification at the second stage.

Preferably, the decomposed fat and/or oil obtained by the first stage partial hydrolysis reaction is less discolored. Specifically, it preferably has such a hue that the 10R+Y [(red value×10)+(yellow value)] thereof, determined by the Lovibond method, is 40 or lower, preferably 30 or lower.

After partial hydrolysis, the oily phase is separated from the aqueous phase by centrifuging or other conventional methods. The glycerol distributed in the aqueous phase can be used in the esterification reaction at the second stage after water has been removed. Alternatively, the reaction mixture may be used as it is in the esterification reaction at the second stage, without separating the oily phase from the aqueous phase.

It is preferred to use the partial decomposition product in the esterification reaction at the second stage without subjecting it to distillation. A treatment for controlling iodine numbers such as hydrogenation or fractionation, may be conducted as long as no trace ingredients are lost.

In the case where a vegetable oil is used as the feedstock, the present method has an advantage that the phytosterol present in the vegetable oil can remain in the final diglyceride product, since the esterification reaction is conducted after partial hydrolysis without a distillation step.

For conducting the second stage esterification reaction, glycerol is added to the partial decomposition product, obtained through the first-stage reaction in such an amount that the mole number of fatty acid groups in the decomposition product mixture of the first stage is from 0.8 to 2.5 mol per 1 mol of glycerol groups based on the total of glycerol groups of the decomposition product mixture of the first stage and glycerol groups added to the second stage.

This reaction is preferably conducted in the presence of an enzyme having an ester activity, such as a lipase or an esterase, preferably in the presence of an immobilized or intracellular lipase having 1,3-position selectivity. Known methods for immobilization are described, for example, In "Koteika Koso (Immobilized Enzyme)," edited by Ichiro Chihata, published by Kodansha Ltd. Publishers, pp. 9–85 and "Koteika Seitai- shokubai (Immobilized Biocatalyst)" edited by Ichiro Chihata, published by Kodansha Ltd. Publishers, pp 12–101. Immobilization onto an ion-exchange resin is preferred. Lipases having 1,3-position selectivity and usable in immobilization include those derived from microorganisms of, for example, the genera Rhizopus, Aspergillus, Mucor, etc., as well as pancreatic lipase, etc. For example, use can be made of the lipases derived from *Rhizopus delemar, Rhizopus japonicus, Rhizopus niveus, Aspergillus niger, Mucor javanicus, Mucor miehei*, etc. A commercial immobilized lipase having 1,3-position selectivity is "Lipozyme IM," manufactured by Novo-Nordisk Bioindustry A.S. An intracellular lipase having 1,3-position selectivity comprises a lipase having 1,3-position selectivity adsorbed or bonded to microbial cells. A commercially available example thereof is "Olipase," manufactured by Nagase & Co., Ltd.

The reaction is conducted in a system to which no water is added other than the water contained in the lipase preparation, the partial decomposition products obtained through the first-stage reaction, glycerol, etc., and to which no other substances such as an organic solvent such as hexane are added.

For accelerating the esterification reaction, it is preferred to remove the water present in and/or generated during the reaction from the reaction system as much as possible. This can be achieved, for example, by passing a dry inert gas through the reaction vessel, by dehydration with a water-absorbent material such as molecular sieves, and by dehydration in a vacuum. The vacuum dehydration method is preferred because it carries less contamination in the reaction system.

Examples of the apparatuses for use include an agitation tank, a fixed bed, and a fluidized tank, combinations of these, etc. Any of batchwise, continuous, and semicontinuous reactions may be conducted.

The reaction products obtained from the second stage esterification reaction are separated from the lipase preparation. The unreacted fatty acids and monoglycerides are removed by conventionally known separation and/or purification means. Thus, high-purity diglycerides can be obtained in high yields. In particular, molecular distillation is effective in separating fatty acids and monoglycerides as the distillate and obtaining a residue comprising a diglyceride-rich composition containing small proportions of triglycerides. Consequently, in this invention, a ratio of diglyceride wt. % to (diglyceride wt. %+triglyceride wt. %)×100 is employed as the definition of diglyceride purity on the assumption that the purity refers to the diglyceride concentration after molecular distillation. According to this invention, diglycerides having a high purity of 80% or higher can be obtained.

The separated lipase preparation can be repeatedly used for the reaction.

EXAMPLES

Having generally described this invention, a further understanding can be obtained by reference to certain specific examples which are provided herein for purposes of illustration only and are not intended to be limiting unless otherwise specified.

EXAMPLE 1

In a 2 liter autoclave, 857 g of refined rapeseed oil "Shirashime-yu" was mixed with 343 g of water and the mixture was hydrolyzed for 10 hours under stirring at 200° C. After completion of the reaction, the reaction mixture was cooled and centrifuged to separate the oily phase from the aqueous phase. Subsequently, 34 g of an immobilized lipase obtained by immobilizing "Lilipase A-10", (manufactured by Nagase & Co., Ltd.,) a lipase having 1, 3-position selectivity and derived from *Rhizopus japonicus,* to a commercial anion-exchange resin (Duolite A- 568: trade name, manufactured by Diamond Shamrock Chemicals) by the immobilizing method described in the Example 1 of JP-A 1-174384, hereby incorporated by reference, was mixed with 300 g of the oily phase obtained through the first-stage reaction and 39 g of glycerol in a four-necked flask (fatty acid groups/glycerol groups=2). The mixture was reacted for 4 hours under stirring at 40° C. while the inside of the system was kept at a pressure of 5 mmHg absolute. Thereafter, the lipase preparation was separated from the reaction product by filtration. Samples of the products of the first-stage reaction and the second-stage reaction were removed, and the amounts of fatty acids were determined by alkalimetry. The samples were trimethylsilylated to determine their compositions with respect to triglycerides, diglycerides, and monoglycerides by gas chromatography. The results are shown in Table 1.

EXAMPLE 2

In a 2 liter autoclave, 857 g of refined rapeseed oil "Shirashime-yu" was mixed with 343 g of water and the mixture was hydrolyzed for 5 hours under stirring at 220° C. After completion of the reaction, the reaction mixture was cooled and centrifuged to separate the oily phase from the aqueous phase. Subsequently, 45 g of the same immobilized lipase as that used in Example 1 was mixed with 400 g of the oily phase obtained through the first-stage reaction and 51 g of glycerol in a four-necked flask (fatty acid groups/glycerol groups=2). The mixture was reacted for 4 hours under stirring at 40° C. while the inside of the system was kept at a pressure of 5 mmHg absolute. Thereafter, the lipase preparation was separated from the reaction product by filtration. The subsequent procedure was conducted in the same manner as in Example 1 to determine the composition of the reaction product. The results are shown in Table 1.

COMPARATIVE EXAMPLE 1

In a 2 liter autoclave, 857 g of refined rapeseed oil "Shirashime-yu" was mixed with 343 g of water and the mixture was hydrolyzed for 4 hours under stirring at 250° C. After completion of the reaction, the reaction mixture was cooled and centrifuged to separate the oily phase from the aqueous phase. Subsequently, 35 g of the same immobilized lipase as that used in Example 1 was mixed with 300 g of the oily phase obtained through the first-stage reaction and 48 g of glycerol in a four-necked flask (fatty acid groups/glycerol groups=2). The mixture was reacted for 4 hours under stirring at 40° C. while the inside of the system was kept at a pressure of 5 mmHg absolute. Thereafter, the lipase preparation was separated from the reaction product by filtration.

The oily phase obtained through the first-stage reaction was then distilled under the conditions of 160 to 250° C. and 1 mmHg or lower to obtain fatty acids. The yield of the fatty acids was 89%. In a four-necked flask were mixed 300 g of this distillation fatty acids, 49 g of glycerol, and 35 g of the same immobilized lipase as that used in Example 1. The subsequent procedure was conducted in the same manner as in Example 1 to determine the composition of the reaction product. The results are shown in Table 1.

EXAMPLE 3

In a four-necked flask were mixed 1,000 g of refined soybean oil, 5 g of a nonselective lipase ("Lipase OF," manufactured by Meito Sangyo), and 500 g of water. The mixture was hydrolyzed for 1 hour under stirring at 40° C. After completion of the reaction, the oily phase was separated from the aqueous phase by centrifugation. Subsequently, 34 g of the same immobilized lipase as that used in Example 1 was mixed with 300 g of the oily phase obtained through the first-stage reaction and 38 g of glycerol in a four-necked flask (fatty acid groups/glycerol groups=2). The subsequent procedure was conducted in the same manner as in Example 1 to determine the composition of the reaction product.

COMPARATIVE EXAMPLE 2

A reaction was conducted under the same conditions as in Example 3 except that 500 g of water in Example 3 was replaced with 100 g of water. The results are shown in Table 1.

The hues of the partial hydrolyzates resulting from the first stages in the above Examples 1 to 3 and Comparative Example 1 were measured by the Lovibond method and quantified in terms of 10R+Y (Red×10 +Yellow). The larger this value is, the worse the discoloration.

Further, the reaction products resulting from the second stages in the above Examples 1 to 3 and Comparative Example 1 were treated by molecular distillation to obtain bleaching diglyceride-rich compositions and the compositions were thereafter subjected to a bleaching treatment, which is an ordinary fat purification treatment. The hues of the compositions thus obtained were measured, and the amounts of phytosterols in the compositions were determined by the following method. The results are shown in Table 2.

As shown in Table 2, the composition obtained by subjecting the partial hydrolyzates resulting from the first stage in Comparative Example 1 to the second-stage reaction without distilling the same had a hue (10R+Y) of 31 even after the bleaching treatment. The color of the composition could not be reduced and remained brown.

Determination of Phytosterol

To 1 g of the oily composition obtained in each step was added 10 ml of a 1N KOH solution in ethanol. After the composition was decomposed by saponification at 80° C. for 1 hour, 15 ml of distilled water was added. Further, 10 ml of n-hexane was added and mixed together with 1 ml of a solution obtained by dissolving cholesterol as an internal reference in n-hexane in a concentration of 10 mg/ml. Thereafter, the hexane layer was sampled and the solvent was removed therefrom. The residue was trimethylsilylated and analyzed by gas chromatography. The amount of the phytosterol was calculated from the area ratio of the cholesterol peak to the phytosterol peak. Although a phytosterol usually coexists with esters of the free sterol with fatty acids, the amount of the free sterol was determined in this analysis because the decomposition was conducted by saponification.

TABLE 2

|  |  | Phytosterol | 10 R + Y (%) |
|---|---|---|---|
| Rapeseed oil |  | 0.57 | 10.1 |
| Soybean oil |  | 0.34 | 5.8 |
| Example 1 | After first-stage reaction | 0.52 | 25.6 |
|  | After purification | 0.42 | 17.2 |
| Example 2 | After first-stage reaction | 0.50 | 24.3 |
|  | After purification | 0.40 | 17.0 |
| Example 3 | After first-stage reaction | 0.30 | 21.0 |
|  | After purification | 0.27 | 16.7 |
| Comparative | After first-stage reaction | 0.48 | 48.3 |
| Example 1 | After purification | 0.35 | 31.0 |
|  | After purification of distilled reaction product | 0.00 | 16.5 |

TABLE 1

|  |  | Fatty acids (%) | Mono-glycerides (%) | Di-glycerides (%) | Tri-glycerides (%) | Di-glyceride purity*[1] (%) | Number of moles of diglycerides per mole of rapeseed oil or soybean oil used |
|---|---|---|---|---|---|---|---|
| Ex. 1 | First-stage reaction | 82.5 | 5.2 | 9.9 | 2.3 |  |  |
|  | Second-stage reaction | 9.7 | 13.1 | 70.2 | 7.0 | 90.9 | 1.06 |
| Ex. 2 | First-stage reaction | 81.6 | 6.4 | 10.6 | 1.3 |  |  |
|  | Second-stage reaction | 10.1 | 13.3 | 69.9 | 6.7 | 91.3 | 1.05 |
| Ex. 3 | First-stage reaction | 74.5 | 1.7 | 10.1 | 13.7 |  |  |
|  | Second-stage reaction | 9.0 | 13.8 | 64.4 | 12.7 | 83.5 | 0.97 |
| Com. Ex. 1 | First-stage reaction | 98.0 | 0.3 | 1.2 | 0.5 |  |  |
|  | Second-stage reaction | 12.3 | 14.0 | 71.6 | 2.1 | 97.2 | 1.08 |
|  | Second-stage reaction after distillation of products of first-stage reaction | 14.2 | 11.1 | 73.1 | 1.6 | 97.9 | 1.09 |
| Com. Ex. 2 | First-stage reaction | 47.4 | 1.8 | 15.3 | 35.5 |  |  |
|  | Second-stage reaction | 5.5 | 14.2 | 53.4 | 26.9 | 66.5 | 0.80 |

*[1]Diglyceride purity; [the ratio of diglyceride wt. % to (diglyceride wt. % + triglyceride wt.%)] × 100
*[2]The yield of fatty acids in the distillation step was 89%

This application is based on Japanese Priority Applications 9-221502 and 10-85576, filed in the Japanese Patent Office on Aug. 18, 1997 and Mar. 31, 1998, respectively, the contents of which are hereby incorporated by reference in their entirety.

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing a diglyceride, comprising the steps of:

conducting a partial hydrolysis by steam decomposition of a fat or oil until the amount of fatty acids reaches 67 to 96% by weight to obtain a partial hydrolyzate;

esterifying said partial hydrolyzate with glycerol after partial hydrolysis, without a distillation step by contacting the fatty acids with glycerol and a lipase or esterase in an amount and under conditions effective to produce a diglyceride in recoverable amounts; and recovering a diglyceride.

2. The process as claimed in claim 1, wherein the esterifying step is performed until a diglyceride purity of at least 80% is reached.

3. The process as claimed in claim 2, wherein the partial hydrolysis is conducted until an amount of decomposed fatty acids reaches 75 to 93% by weight.

4. The process as claimed in claim 1, wherein the partial hydrolysis is conducted at 190 to 240° C. by steam decomposition.

5. The process as claimed in claim 1, wherein the partial hydrolysis is carried out in the presence of an amount of water in a range from 20 to 180 parts by weight per 100 parts by weight of the fat or oil.

6. The process as claimed in claim 1, wherein the partial hydrolyzate has a hue such that the 10R+Y value thereof is 40 or lower as measured by the Lovibond method.

7. The process as claimed in claim 1, wherein the fat or oil used in the partial hydrolysis is a member selected from the group consisting of vegetable fats, vegetable oils, animal fats, animal oils, and mixtures thereof.

8. The process as claimed in claim 1, wherein the fat or oil used in the partial hydrolysis is a member selected from the group consisting of rapeseed oil, soybean oil, cottonseed oil, olive oil, corn oil, coconut oil, beef tallow, lard, fish oil and mixtures thereof.

* * * * *